United States Patent
Bruza et al.

(10) Patent No.: US 11,771,323 B2
(45) Date of Patent: Oct. 3, 2023

(54) OPTICAL TIME-OF-FLIGHT IMAGING METHODS AND SYSTEMS FOR SURGICAL GUIDANCE AND FLUORESCENCE DEPTH ESTIMATION IN TISSUE

(71) Applicant: THE TRUSTEES OF DARTMOUTH COLLEGE, Hanover, NH (US)

(72) Inventors: Petr Bruza, Lebanon, NH (US); Brian Pogue, Hanover, NH (US)

(73) Assignee: THE TRUSTEES OF DARTMOUTH COLLEGE

(*) Notice: Subject to any disclaimer, the term of this patent is extended or adjusted under 35 U.S.C. 154(b) by 0 days.

(21) Appl. No.: 17/794,297

(22) PCT Filed: Nov. 15, 2021

(86) PCT No.: PCT/US2021/059420
§ 371 (c)(1),
(2) Date: Jul. 21, 2022

(87) PCT Pub. No.: WO2022/104228
PCT Pub. Date: May 19, 2022

(65) Prior Publication Data
US 2023/0047584 A1 Feb. 16, 2023

Related U.S. Application Data

(60) Provisional application No. 63/114,049, filed on Nov. 16, 2020, provisional application No. 63/113,914, filed on Nov. 15, 2020.

(51) Int. Cl.
*G01N 21/64* (2006.01)
*A61B 5/00* (2006.01)

(52) U.S. Cl.
CPC ....... *A61B 5/0071* (2013.01); *G01N 21/6408* (2013.01); *G01N 21/6458* (2013.01)

(58) Field of Classification Search
CPC .... G01N 21/6428; G01N 21/76; G01N 33/50; G01N 21/645; G01N 2015/0065;
(Continued)

(56) References Cited

U.S. PATENT DOCUMENTS 6,377,842 B1 4/2002 Pogue et al.
2002/0139920 A1 10/2002 Seibel et al.
(Continued)

OTHER PUBLICATIONS

International Patent Application No. PCT/US2021/059420, International Search Report and Written Opinion dated Mar. 10, 2022, 12 pgs.

*Primary Examiner* — Deborah L Malamud
(74) *Attorney, Agent, or Firm* — Cozen O'Connor

(57) ABSTRACT

A system and method for depth-resolved imaging of fluorophore concentrations in tissue uses a pulsed light source stimulus wavelength to illuminate the tissue; and a time-gated electronic camera such as a single-photon avalanche detector camera to observe the tissue in multiple time windows after start of each light pulse. A filter-changer or tunable filter is between the tissue and the electronic camera with fluorescent imaging settings and a stimulus wavelength setting, and an image processor receives reflectance images and fluorescent emissions images from the time-gated camera and processes these images into depth and quantity resolved images of fluorophore concentrations in the tissue.

10 Claims, 13 Drawing Sheets

(58) Field of Classification Search
CPC ...... G01N 33/483; G01N 21/62; G01N 21/63; G02B 21/0076; G02B 21/0064; G02B 21/64; A61B 5/0071
See application file for complete search history.

(56) References Cited

U.S. PATENT DOCUMENTS

2009/0137908 A1    5/2009   Patwardhan
2011/0275932 A1   11/2011   Leblond et al.

SPAD array

- Gating and single photon sensitivity native to SPAD gated CMOS sensor

- Need to control photodiode sensitivity to enable gating (micro-integrations)
- Need to improve single photon sensitivity Distribution of time offsets (μ)

Distribution of kernel widths (σ)

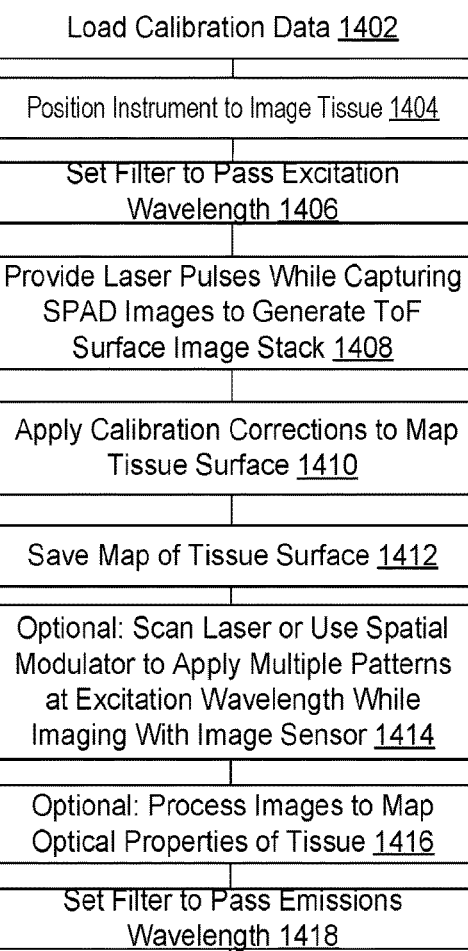
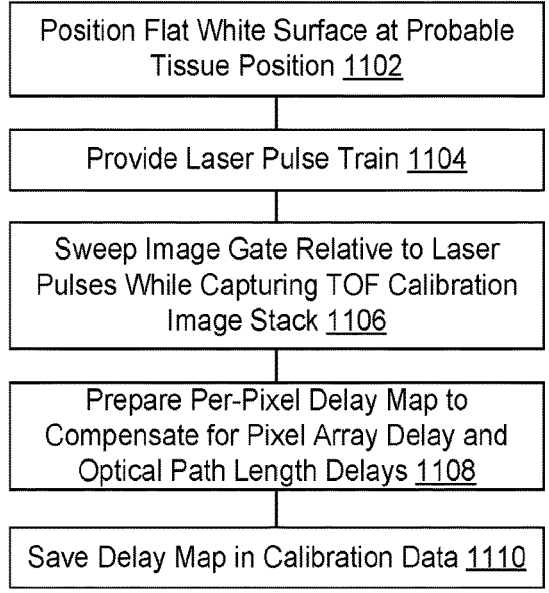
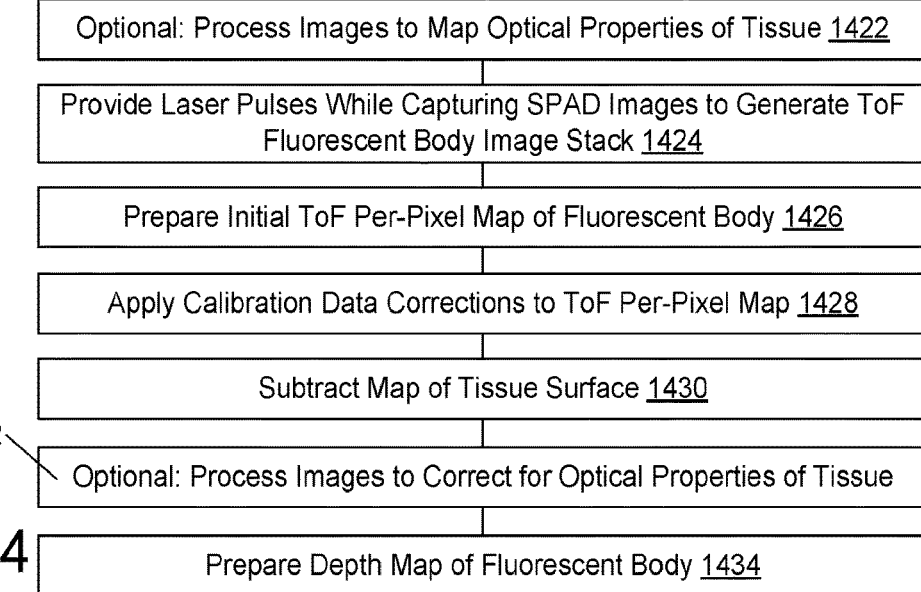
Fig. 13
Fig. 14

OPTICAL TIME-OF-FLIGHT IMAGING METHODS AND SYSTEMS FOR SURGICAL GUIDANCE AND FLUORESCENCE DEPTH ESTIMATION IN TISSUE

PRIORITY CLAIM

This application is a 35 U.S.C. § 371 filing of International Application No. PCT/US2021/059420, filed 15 Nov. 2021, which claims priority to U.S. Provisional Patent Application 63/113,914 filed 15 Nov. 2020, and to U.S. Provisional Patent Application 63/114,049 filed 16 Nov. 2020. The entire content of each of these patent applications is incorporated herein by reference.

GOVERNMENT RIGHTS

This invention was made with government support under R01 EB023909 awarded by the National Institutes of Health. The Government has certain rights in the invention.

FIELD

The present application relates to the fields of surgery and imaging of surgical sites. In particular, the present application relates to optical imaging using fluorescence and optical time-of-flight information to assist a surgeon in distinguishing tissue types during surgical procedures, for example, tumor resection.

BACKGROUND

There are many types of lesions treatable with surgical removal or modification. These lesions include abnormal tissues in any location in the body, such as malignant (or cancerous) tumors, and many slower-growing "benign" tumors. These lesions also include tissues abnormal for their location in a particular organ, but resembling normal tissues found in other locations in the body. Other lesions may incorporate material foreign to the body, including bacteria, viruses, or parasites, and associated zones of immune reactions. Still others involve developmental anomalies, such as arteriovenous malformations and berry aneurisms. Other lesions may incorporate scars and adhesions from prior illness or injury. While lesions are of many kinds, it is generally desirable for a surgeon to be able to visualize the lesion being treated and to be able to discriminate between normal and lesion tissues.

Generally, surgeons treat lesions that are visible to them during surgery. At times, lesions and tumors may lie under the surface of an organ, or under a visible and exposed surface of an operative site, where they may be obscured by overlying tissue and not readily visible, or may have poor contrast relative to surrounding stroma. It is desirable to make these lesions, including portions of malignant tumors, visible to a surgeon so that they can be more readily treated with less normal overlying tissue damaged during treatment.

It is known that some fluorescent compounds will accumulate in tumors and other abnormal tissues. Fluorescence-based medical imaging has been proposed for detecting and mapping tumors and other abnormal tissues in organs such as, but not limited to, breast and brain; in particular, fluorescence-based imaging is believed to be useful in identifying abnormal tissues during surgery so that a surgeon may remove more abnormal tissue while avoiding damage to nearby normal tissues.

For a surgeon to properly treat lesions and other abnormal tissues, the surgeon must locate them during surgery. Further, for surgeons to avoid unintended damage to other nearby structures, it may also be necessary to locate particular portions of those other structures precisely during the surgery.

It is desirable to find improved ways of locating and identifying during surgery abnormal tissue, including tissue both abnormal for the organ and malignant tissue, including small invasive branches of tumors in tissue adjacent to tumors.

SUMMARY OF THE EMBODIMENTS

In a first aspect, a method of providing surgical guidance, fluorescence depth estimation, and fluorophore concentration estimation in tissue includes resolving subsurface depth of a fluorescent object embedded in tissue using a two-dimensional, time-of-flight light sensor.

In a second aspect, a method of estimating depth and shape of a fluorescence-tagged target and fluorophore concentration, includes using reflectance-based tissue optical property measurement to calibrate the response of time-of-flight-based depth on varying tissue optical properties.

In a third aspect, a method of estimating depth and shape of a fluorescence-tagged target and fluorophore concentration includes combining pulsed structured light illumination with time-of-flight camera acquisition to improve accuracy of depth localization and shape evaluation using the presented technology claims.

In a fourth aspect, a method of estimating depth and shape of a fluorescence-tagged target and fluorophore concentration includes calculating the depth of fluorescent object in each pixel within a field of view of the presented time-of-flight camera, using temporal profiles of fluorescence and diffuse reflectance, in conjunction with surface map.

In a fifth aspect, estimating depth and shape of a fluorescence-tagged target and fluorophore concentration includes estimating true fluorophore concentration and shape of the fluorescent object embedded in tissue (such as tumor), using the information provided by time-of-flight camera.

In a sixth aspect, a system for estimating depth and shape of a fluorescence-tagged target and fluorophore concentration includes a pulsed light source emitting a wide-field illumination pattern onto the object which has a fluorescent target located at a certain depth under the surface, and one or more time-gated cameras detecting the diffusively reflected light at one wavelength band $\Lambda_{EX}$, and fluorescent light at a wavelength band of the fluorescence emission $\Lambda_{EM}$.

In another aspect, an instrument for performing time of flight surface mapping and fluorescent depth estimation includes a pulsed laser operable at a fluorescent stimulus wavelength coupled through a first optical device to provide illumination to an imaging optical system, the imaging optical system configured to provide light to tissue and to receive image light from the tissue; the imaging optical system coupled to provide image light through a filter device and to a single-photon avalanche detector (SPAD) image sensor, the SPAD image sensor coupled to provide high time resolution images to an image capture unit; an image processor coupled to receive images from the image capture unit and to process received images according to code in a memory and to provide images to a display; where the first optical device is selected from the group consisting of a lens configured to couple light to an efferent optical fiber, and a dispersive lens; where the pulsed laser provides pulses of less than 100 picoseconds risetime and less than 100 nanoseconds width, and the SPAD sensor has a gate time resolution of less than 100 picoseconds programmable by the image processor; where the image processor is configured by the code to set the filter device to pass the fluorescent stimulus wavelength, to receive a stimulus image stack comprising a plurality of SPAD images of the tissue taken at time increments of the SPAD sensor gate time resolution, to set the filter to pass a fluorescent emissions wavelength while blocking the fluorescent stimulus wavelength, to receive an emissions image stack comprising a plurality of SPAD images of the tissue taken at time increments of the SPAD sensor gate time resolution, to process the stimulus image stack into a surface map of the tissue, and to process the emissions image stack into a map of depth of fluorophore in the tissue; and where the imaging optical system is an optical system selected from a microscope optical system and an endoscope optical system.

BRIEF DESCRIPTION OF THE FIGURES

FIG. 13 is a flowchart of preparing a calibration map for use in compensating for gate skew and optical path variations, in embodiments.

FIG. 14 is a flowchart illustrating operation of a system incorporating an embodiment.

DETAILED DESCRIPTION OF THE EMBODIMENTS

An optical imaging system utilizes optical time-of-flight (TOF) information to estimate depth and shape of tissue, and of fluorophore-tagged "targets," such as tumor tissue or an implant, embedded within a non-fluorescent scattering media, such as healthy tissue. The system captures multi-wavelength time-of-flight information to calculate topological shape of the fluorophore concentrations at the target's surface, the optical properties of the target, and depth of embedded fluorophore. The method uses this depth information to estimate the shape of the fluorescent target, and absolute concentration of fluorophore. The system provides information of the depth and shape of the target to users, such as surgeons, to guide procedures involving the fluorophore concentrations, such as fluorescence-guided surgery. The system provides the depth, shape, and concentration information in vivo or ex vivo. The method utilizes additional information about the spatio-temporal fluorophore distribution and optical properties of the tissue obtained through using structured light illumination to improve accuracy of depth, shape and concentration of fluorophore. The method also uses TOF information to distinguish primary fluorescence signals from reflected secondary signals.

Imaging System

Figure 1A:
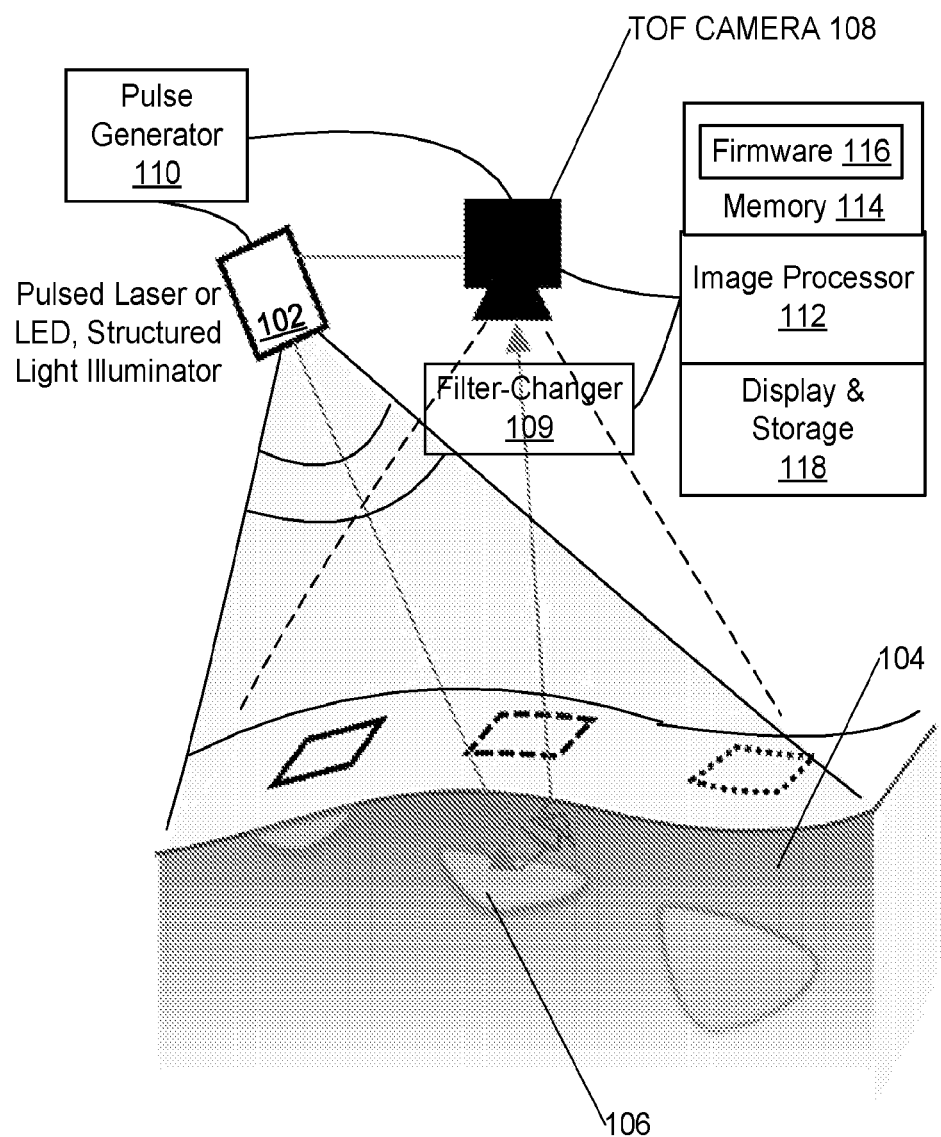
FIG. 1A depicts a block diagram of an embodiment of an optical imaging system.

A block diagram of an optical imaging system 100 is shown in FIG. 1A. A pulsed light source 102, typically a pulsed laser, emits a wide-field illumination pattern of fluorescent stimulus light onto an object 104 which has embedded within it a fluorescent target 106 having a fluorophore concentration located at a depth under the surface of object 104. The object is typically formed of a turbid optical media that tends to scatter light such as human or animal tissue. At least one time-gated camera 108 detects the diffusively reflected light at one wavelength band of the stimulus light $A_{EX}$. Either a second time-gated camera, or the same time-gated camera 108 using a different filter of a filter-changer 109, or a different setting of a tunable filter, detects fluorescent emissions light at a wavelength band of the fluorescence emission $A_{EM}$. A pulse generator 110 controls both light source 102 and camera 108 to cause the camera to capture a sequence, or "stack," of image frames, where the duration of each frame is very short, typically few nanoseconds, and where each frame in the sequence is captured at a different temporal delay after an associated light pulse emitted by the light source.

In an alternative embodiment 150, time-of-flight and reflectance cameras are separated. A time-of-flight fluorescence camera 152 is equipped with a fluorescent emissions filter 154 configured to block fluorescent stimulus wavelength light, and a separate reflectance camera 156 is provided that has a reflectance filter configured to pass fluorescent stimulus wavelength light.

In embodiments, the light source incorporates a structured-light modulator, also known as a spatial modulator, such as a micromirror array, the structured-light or spatial modulator, such as a digital micromirror device, operable under control of an image processor 112 to provide structured light with multiple patterns, the multiple patterns including patterns having spatial modulation at each of multiple spatial frequencies with each spatial modulation pattern frequency being provided at multiple phase offsets. In particular embodiments, each spatial modulation pattern frequency is provided at three distinct phase offsets, and two or more spatial frequencies are used. Images may be obtained of the object at each combination of phase offset and spatial frequency and is processed—as we have previously demonstrated—to map optical properties of the object.

Pulsed light source 102 outputs a beam of light with pulsewidth of less than a microsecond, and in an embodiment less than 100 nanoseconds, pulsewidth with rise or fall time between 10% to 90% intensity of each pulse below 1 ns. Pulsed light source 102 in a particular embodiment operates with megahertz repetition rate. In an embodiment, the camera electronic shutter is gated such that it is effectively open for a five to 15 nanosecond interval that can be shifted relative to each laser light pulse in increments of from 10 through less than 20 to less than 100 picoseconds, and in a particular embodiment 17 picoseconds, across the laser light pulses. In some embodiments, camera 108 is an intensified camera capable of real-time background subtraction and noise filtering capability.

Figure 2:
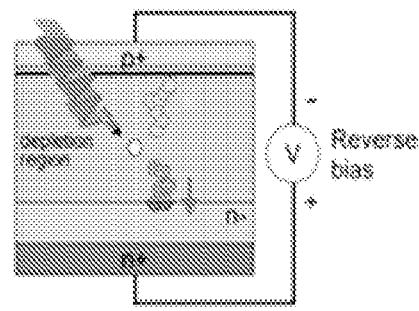
FIG. 2 is a schematic block diagram of a single-photon avalanche diode, in embodiments.

In an embodiment, time-gated camera 108 uses a single-photon avalanche diode (SPAD) array. A single SPAD array is shown schematically in FIG. 2. Each single photon initiates an avalanche in a photodiode of nearly infinite gain, which implies that the pixel needs to be switched off and recharged before it can sense another photon. This takes so called dead time, and it limits an achievable dynamic range within the microsecond window within which images are captured. For example, if a typical dead time is 60 ns, and pulse duration 6 us, we have a theoretical dynamic range of 100. However, to prevent pileup, the pixel should operate at light levels well below this limit. For example, in time correlated single photon counting, an acceptable limit is 5-10% of the theoretical dynamic range, meaning we can count just few tens of photons per frame. An advantage of SPAD cameras is very fast rise and fall gating times of less than 1 ns, and sharp gating rise and fall times that improve depth estimation accuracy. In embodiments, the SPAD array gate, or electronic shutter, is effectively open for between five to 15 nanoseconds and is effectively open for a time window that can be shifted relative to each laser light pulse in increments of from 10 through less than 20 to 100 picoseconds, and in a particular embodiment 17, picoseconds, across the laser light pulses.

Figure 3:
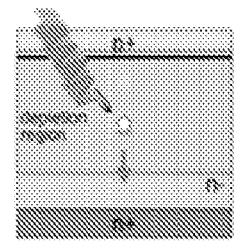
FIG. 3 is a schematic block diagram of a gated CMOS sensor, in embodiments.

In alternative embodiments, time-gated camera 108 uses time-gated complementary metal-oxide-semiconductor (CMOS) sensors as shown in FIG. 3. Special timing circuitry drives the transfer and PD reset transistors, to allow repetitive micro integrations of charge on each photodiode, before read-out of each pixel. In principle, the photodiodes are held in a reset state for most of each cycle, and only during a gate period during and immediately after each light pulse is emitted is it allowed to transfer charge to a storage capacitor. Because of very limited gain of this type of pixel, typically just 4× or so, the useful signal may be buried within noise electrons which have been thermally excited and trapped in the capacitor unless illumination is much brighter than used with SPAD array.

In alternative embodiments, time-gated camera 108 uses a dual-tap approach, where light is collected in two consecutive temporal bins, each of duration of less than 3 nanoseconds. The ratio of the signals from each bin can be used to estimate the slope of fluorescence rising or falling edge, which is a parameter useful for depth estimation.

Time-gated camera 108 feeds images to an image processor 112 having a memory 114. Memory 114 contains a code or firmware 116 having machine-readable instructions for performing structured-light extraction of optical parameters from tissue and for performing the method for depth estimation of fluorophore concentrations herein described. In some embodiments, the image processor 112 is configured to output tomographic images illustrating depth of the fluorophore concentrations on a display 118.

Method for Depth Estimation

Figure 6:
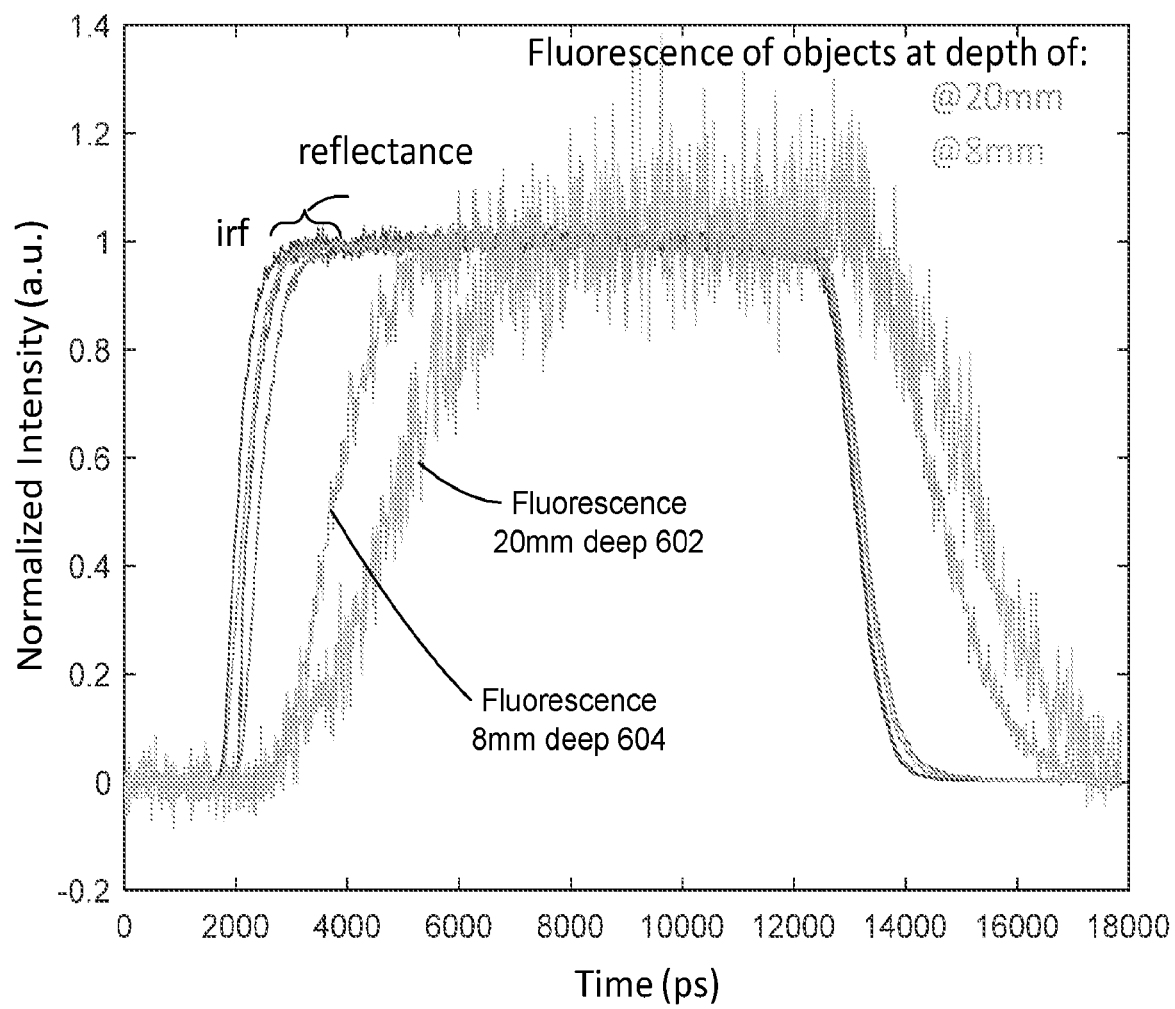
FIG. 6 is a graph illustrating observed intensity versus time of reflected stimulus light and fluorescent emissions as observed at two depths in tissue.

Fluorescent emissions from fluorophore concentrations at greater depths in turbid media such as tissue, such as 20 millimeters 602 (FIG. 6), are significantly delayed from fluorescent emissions from concentrations of the same fluorophore at shallower depths in tissue, such as 8 millimeters 604. FIG. 6 shows light emissions at various depths in turbid media using IRDye680. Similar results are expected with other fast fluorophores such as other dyes in the IRDye family, and particularly good results with the indocyanine green (ICG) that is often used in medical fluorescence imaging; fast fluorophores with decay times of 1 ns or less are expected to give the best results. Medium-fast fluorophores with decay time constants of under 20 nanoseconds, including Protoporphyrin IX (PpIX), a fluorophore generated in tissue through metabolizing of aminolevulinic acid, are expected to give reasonably good results at shallow depths in tissue despite the 5-16 nanosecond fluorescence decay time of PpIX.

The system used to obtain the data illustrated in FIG. 6 includes a laser with pulse width under 100 picoseconds and a camera with a 12-nanosecond electronic shutter period that was delayed incrementally in 17-picosecond steps to shift the window across the laser pulse and observe fluorescent emissions near both the rising and falling edges of the laser pulse.

Image sequences, also known as image stacks, acquired by time-gated camera 108 are processed to determine time of arrival of fluorescent emissions and to estimate fluorescence depth in tissue from the determined time of arrival of the fluorescent emissions. In embodiments, the determined time of arrival is resolved to less than one nanosecond, and in particular embodiments the determined time of arrival is resolved to less than one hundred picoseconds, twenty picoseconds, or ten picoseconds. In embodiments, a representative gating sequence accumulates signal from a dozen of pulses, followed by background frame acquisition. This method of recording—a time-gated TOF imaging-produces an image sequence where information about temporal profile of the reflected light and fluorescence signal is provided for each pixel. The captured reflectance and fluorescence image sequences are corrected for an instrument response function (IRF) of the imaging system (including correction for optical path variations and image skew as described below), and used to extract the surface topology and tissue optical properties, and depth of fluorescence, respectively.

The reflectance image sequence is also used to estimate the surface topology of the object by measuring the time delay between light pulse emission and time of arrival of the reflected stimulus-wavelength light pulse. In one embodiment, this time delay is estimated as a difference between $T_0$, indicated by maximal gradient of the rising edge of the light pulse as it leaves the light source, and $T_R$, time of the maximal gradient of the received reflectance pulse. By measuring the time delay of signal detected by each pixel, and considering speed of light, surface topology is extracted. This surface topology is subsequently used as a reference surface, from which the depth of fluorescence object is estimated.

Figure 11:
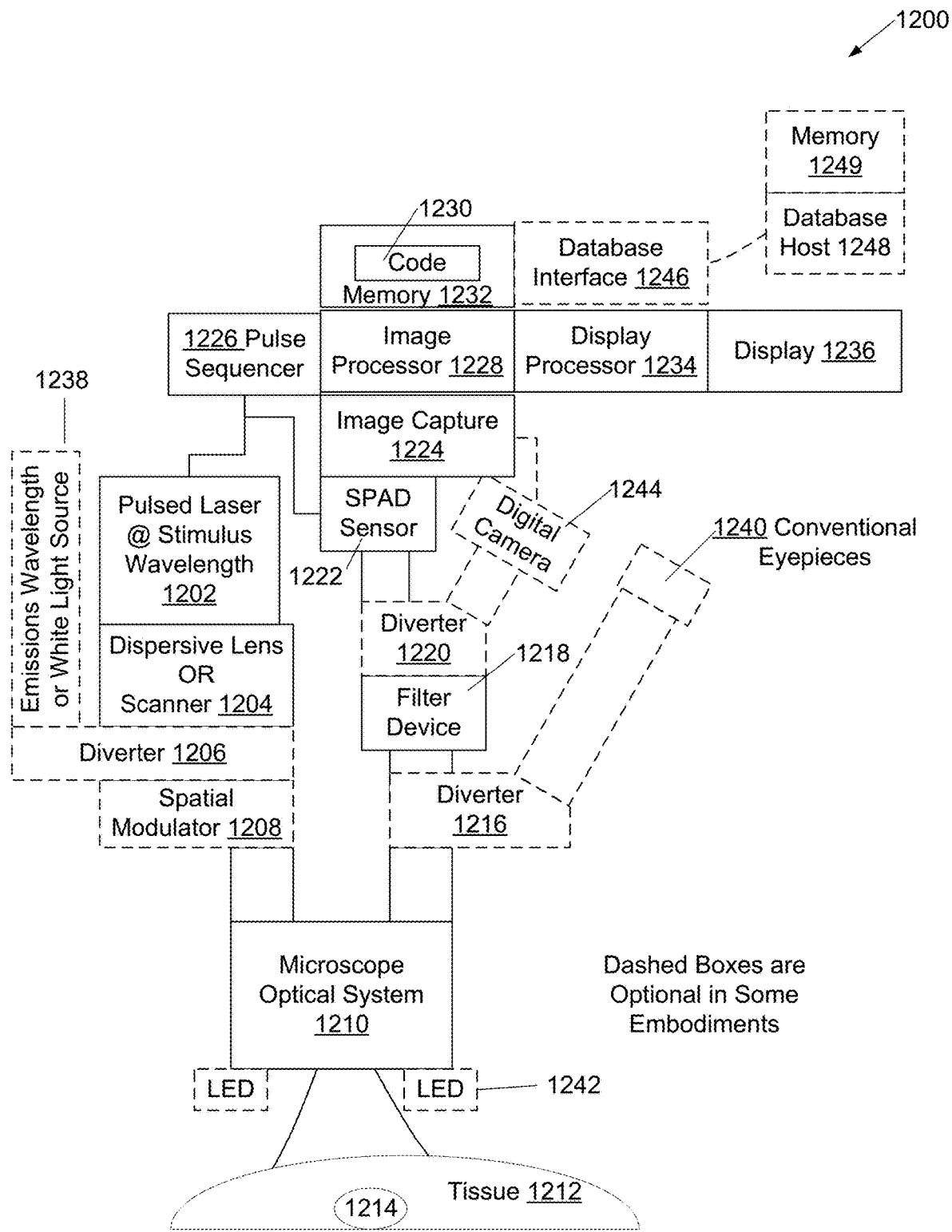
FIG. 11 is a block diagram of an embodiment incorporated into a surgical microscopy system.

Further, the reflected light is used to estimate absorbance and effective scattering coefficient of the tissue. The reflected light pulse is temporally delayed and blurred due to the scattering in the media surrounding the target, and target itself. The extent of this temporal blurring is proportional to the scattering properties of the media. In one embodiment, a model assumes that detected reflectance signal has a temporal profile of the IRF, convolved in time with a blurring function, whose parameters are directly proportional to the tissue optical properties—absorption coefficient, and scattering coefficient. These parameters are used to estimate the depth of florescence in the next step. In some embodiments, these absorption coefficient and scattering coefficient parameters are also estimated from digital processing of images of blur of spatially-modulated light. In these embodiments, a spatial modulator, as shown in FIG. 11, is used to project patterned light of a particular wavelength at least three phases of a first spatial frequency while reflectance images are obtained at that particular wavelength. These reflectance images are then analyzed for spatial blur to determine the absorption coefficient and scattering coefficient of the tissue. We note that this process may be performed at multiple spatial frequencies each with the particular wavelength set for fluorescent stimulus and emissions wavelengths because these differ with wavelength in tissue. In some embodiments, the absorption coefficients and scattering coefficients used for time-of-flight depth estimation of fluorophore concentrations are determined as a weighted average of coefficients determined from time blur with those determined from spatial blur.

The fluorescence signal, detected at $\Lambda_{EM}$, is also temporally blurred as seen in FIG. 6. Here, one embodiment assumes that the fluorescence temporal profile has a temporal profile of the IRF convolved in time with the reflectance blurring function, and further convolved with a fluorescence propagation blurring function. Here, the parameters of fluorescence propagation blurring function are extracted and assumed proportional to the depth of fluorophore concentrations emitting the fluorescence signal. In another embodiment, a calibration look-up table is created for varying reflectance blurring parameters and fluorescence propagation blurring functions to rapidly estimate depth of the emitting fluorophore concentrations of the target.

Figure 4:
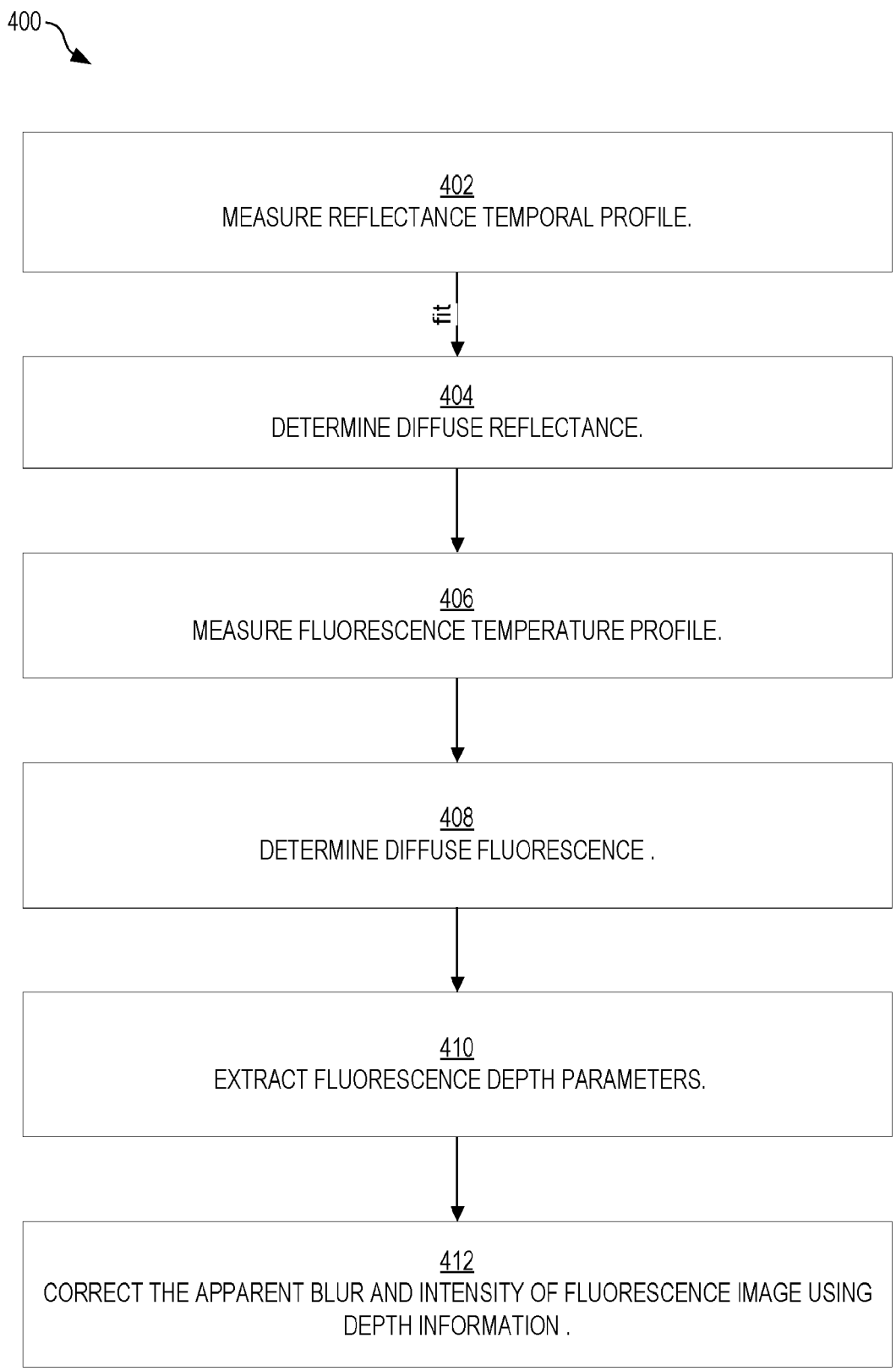
FIG. 4 is flowchart of a method of depth estimation using optical time-of-flight imaging, in embodiments.

FIG. 4 is a flowchart of a method 400 of depth estimation using optical time-of-flight imaging, in embodiments.

Step 402 includes measuring a reflectance temporal profile. In an example of step 402, a reflectance temporal profile is used to estimate surface topology by measuring the time delay between light pulse emission and time of arrival of the reflected light pulse. In one embodiment, this time delay is estimated as a difference between $T_0$, indicated by maximal gradient of the rising edge of the light pulse, and $T_R$, time of the maximal gradient of the received reflectance pulse.

Step 404 includes determining diffuse reflectance. In an example of step 404, a convolution of the instrument response function (IRF) is fit with eq. 1 and parameters $C_1$, $C_2$ and $C_3$ are extracted.

$$I_R \cong C_1 t^{-\frac{3}{2}} \exp(-C_2 t) \exp\left(-\frac{C_3}{4}\right) \quad [1]$$

Step 406 includes determining a fluorescence temporal profile. In an example of step 406, a fluorescence profile is detected by time-gated camera 108 at $\Lambda_{EM}$.

Step 408 includes determining diffuse fluorescence. In an example of step 408, parameters $C_1$, $C_2$ and $C_3$ are entered in eq. 2 and its convolution with IRF is fit to the fluorescence data of step 406.

$$I_F \cong C_1 t^{-\frac{3}{2}} \exp(-C_2 t) \left[ C_4 \exp\left(-\frac{C_4^2}{t}\right) - C_5 \exp\left(-\frac{C_3^2}{t}\right) \right] \quad [2]$$

Step 410 includes extracting fluorescence or fluorophore concentration depth parameters. In an example of step 410, parameters $C_4$ and $C_5$ are extracted where $C_4$ and $C_5$ linearly depend on depth. Depth of the fluorophore concentrations is estimated from $C_4$ and $C_5$.

Step 412 includes correcting apparent blur of fluorescence image. In an example of step 412, the apparent blur and intensity of fluorescence image is corrected using depth information from step 410.

In embodiments, some of the steps in method 400 are simplified by using a lookup table to improve speed.

Figure 1B:
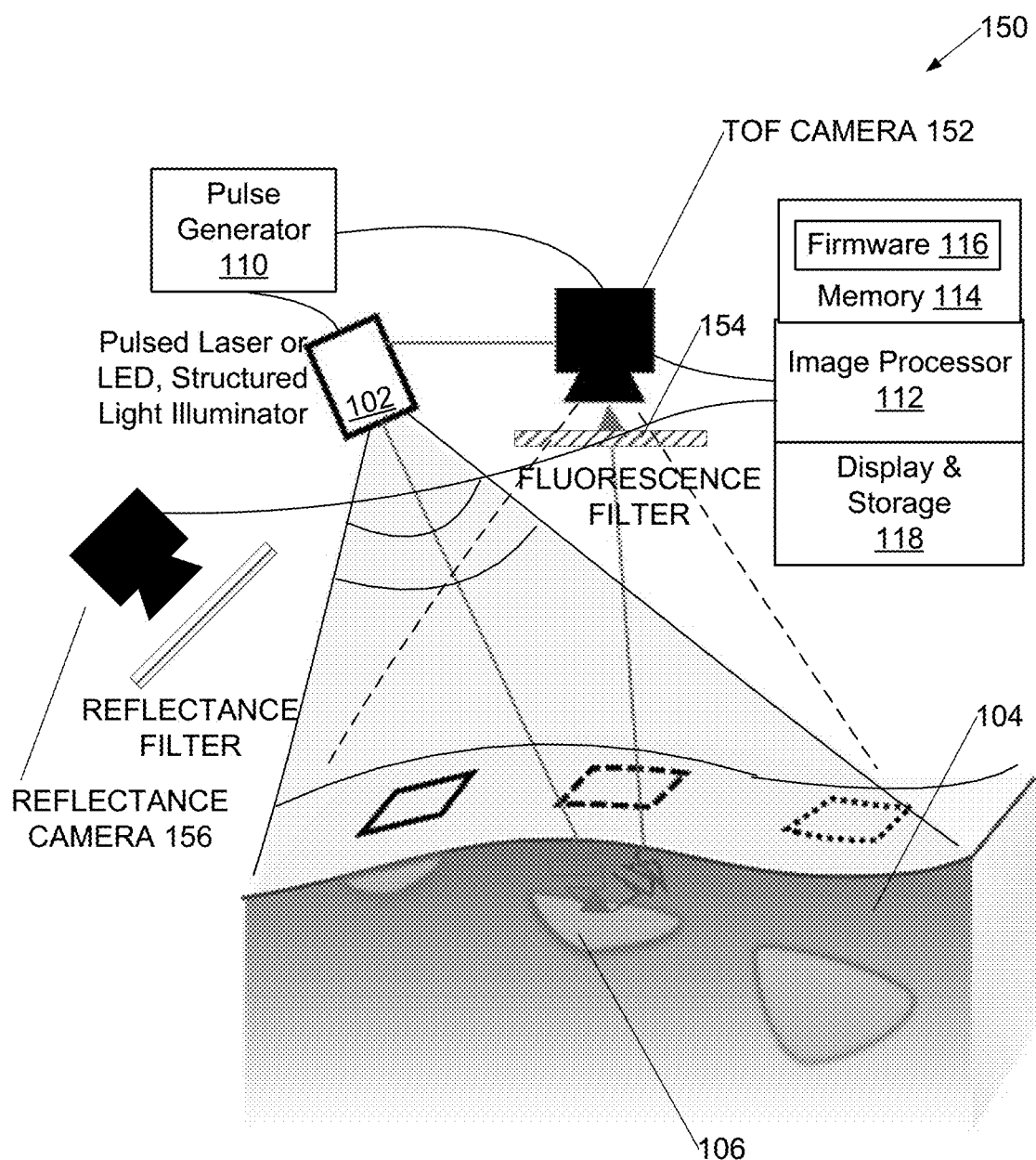
FIG. 1B is a block diagram of an alternative embodiment of an optical imaging system.
Figures 5A, 5B:
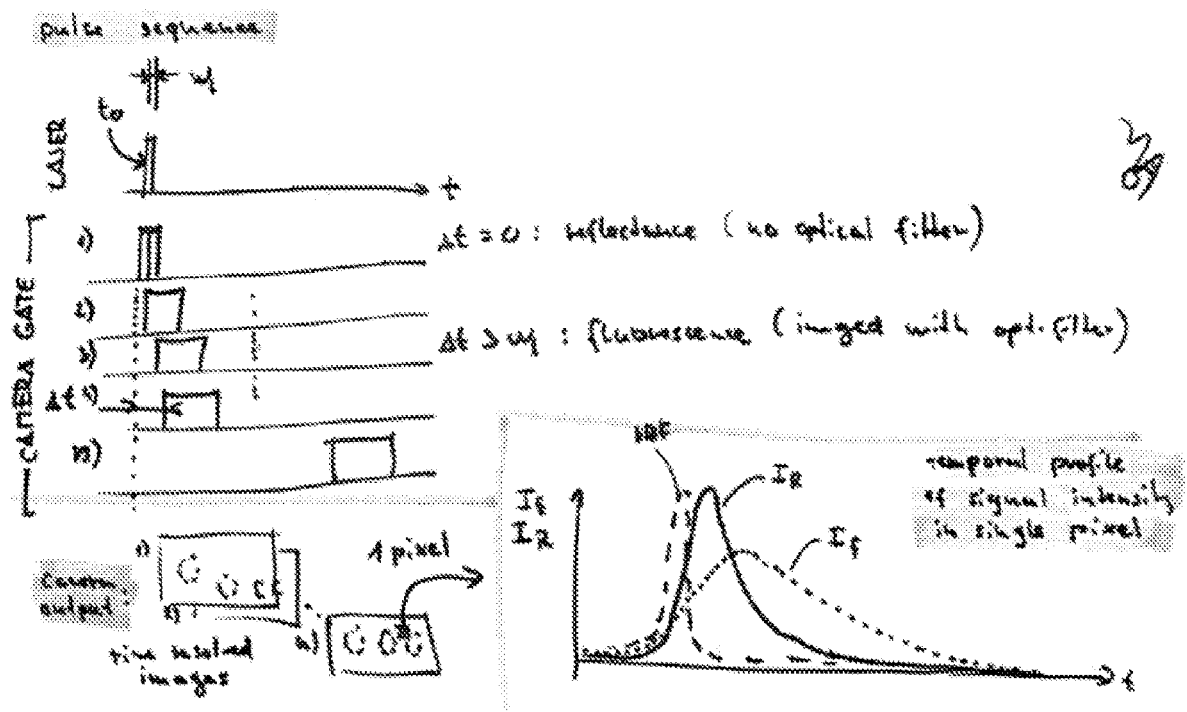
FIG. 5A illustrates a pulse sequence for an optical imaging system of FIG. 1A, in embodiments.
FIG. 5B illustrates a representative temporal profile determined from a pulse sequence of FIG. 5A.

In embodiments, FIG. 5A illustrates a pulse sequence for light source 102 and time-gated camera 108 of FIG. 1. FIG. 5B also illustrates a representative temporal profile determined from a pulse sequence of FIG. 5A.

In embodiments, an optical time-of-flight (ToF) imaging method and system for surgical guidance and fluorescence depth estimation in tissue uses 2D remote imaging of both diffuse reflectance and fluorescence with a ToF camera, applying the reflectance-based parameters to elucidate depth of tagged objects using time-resolved fluorescence images. This method is used to correct the fluorescence image brightness (which is apparent fluorophore concentration) to counteract tissue absorption effects.

The distance measured between the camera/laser and tissue may be used to compensate images for the inverse square law that governs excitation light transport and absorption in tissue. In fluorescence guided surgery, this inverse square law absorption makes the assessment of fluorophore concentration challenging. The surgeon sees an object at different brightness depending on the distance of surgical microscope (or endoscope) and depth of the object in tissue, and that in turn causes the observed fluorescence margins to appear smaller or wider, depending on distance. This can cause false negative or false positive assessment. With real-time ToF distance measurement to compensate images, the margins can be more accurately rendered to the surgeon at any distance of the laser/camera head and depth in tissue.

Because light path lengths differ across images, the image processor 112 must compensate images for time delays associated with the path lengths. This delay compensation is achieved through a calibration process.

The speed of light in vacuum is approximately $3 \times 10^8$ meters per second. Dividing by 2 and multiplying by 10 picoseconds ($10^-$second) time resolution gives $1.5 \times 10^{-3}$ meter, or 1.5 millimeters resolution attainable in a vacuum; we note, however, the speed of light in aqueous media, including turbid media, is reduced below the speed of light in vacuum. Even more importantly, multiple scattering in turbid media leads to a substantial slowing down of the transmitted flux, which can be characterized as propagation by diffusion.

In addition to optical path variations, there are on-chip delays that must be compensated for. Some SPAD sensor arrays, such as a 1 megapixel array announced by Canon in June 2020, may have as much as a 400 picosecond "position skew", or variation in gate signal arrival time between SPAD sensor pixels at array center and SPAD sensor pixels at array periphery. This position skew is a result of resistance-capacitance (RC) delays along gate signal lines within the SPAD sensor array; if not compensated for 400 picoseconds could produce a 60 millimeter error in mapping surfaces with the system.

To correct for optical path variations and position skew, a flat surface is positioned (1102, FIG. 11) in view of the instrument at a probable tissue location, then project pulses 1104 of spatially-unmodulated light from the pulsed laser while sweeping 1106 the gate signal in approximately 10 picosecond increments to obtain a stack of uncalibrated SPAD images. An image is determined for each pixel where that pixel first shows response to the pulsed laser in the stack of uncalibrated SPAD images, the count in the image stack for that first response for each pixel is used to create 1108 a calibration delay map that is saved 1110 and used to correct for gate position skew and optical path differences when mapping tissue surfaces and mapping fluorescent body depths with the system. Correction for gate position skew and optical path differences may be performed by subtracting the calibration delay map from delay maps generated while observing tissue.

High spatial frequency (HSF) structured light imaging (SLI), has shown distance and depth free sensitivity to changes in freshly resected breast morphology over a large field of view (FOV). This approach, originally termed spatial frequency domain imaging (SFDI), has advantage of structured illumination ability to tune depth sensitivity with the spatial modulation frequency. While the contrast at low spatial frequencies is dictated by absorption features (presence of blood, fat) s and diffuse scattering (density of tissue), the contrast of sub-diffusive high spatial frequency images is dictated by both scattering intensity and the angular distribution of scattering events, or phase functions, as photon propagation is constrained to superficial volumes with minimal volumetric averaging over tortuous photon path-lengths. The phase function arises from the underlying physical properties of tissue ultrastructure. Recent studies used sub-diffusive structured light imaging to quantify angular scattering distributions through the phase function parameter γ, which is related to the size-scale distribution of scattering features. This phase function parameter γ, along with the reduced scattering coefficient $\mu'_s$, was used to cluster benign and malignant breast tissue pathologies in freshly resected human breast specimens and morphologies within murine tumors, as different tissue morphologies with unique densities and size-scale fluctuations manifest unique light scattering properties.

Although SLI can generate wide-field images of the specimen surface, it is unable to provide high resolution (<1 mm) depth contrast or a tomographic reconstruction through the specimen volume.

Figure 7:
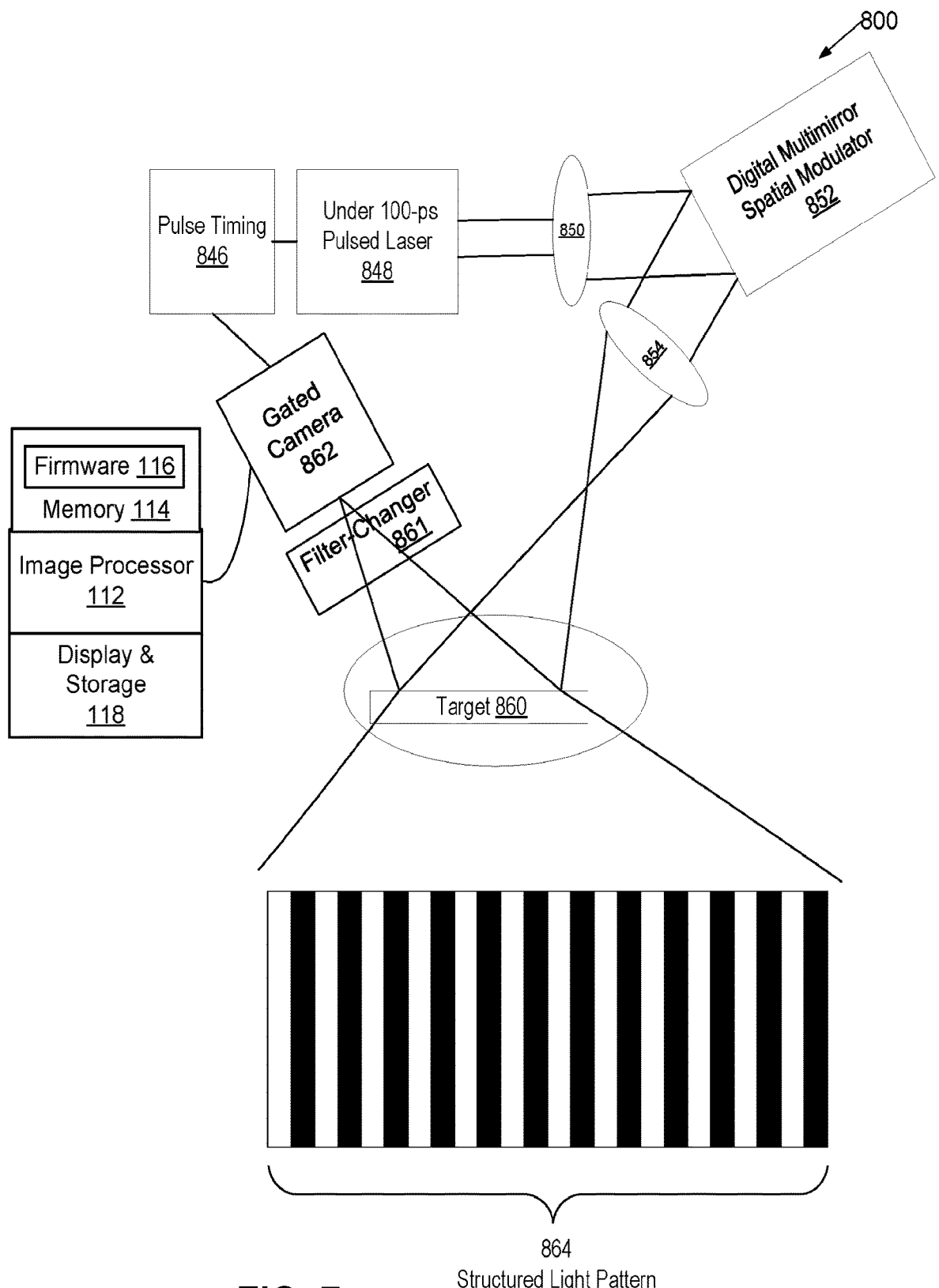
FIG. 7 is a block diagram of an embodiments of an optical imaging system, combining the pulsed laser time-of-flight sensor with structured light illumination.
Figure 8:
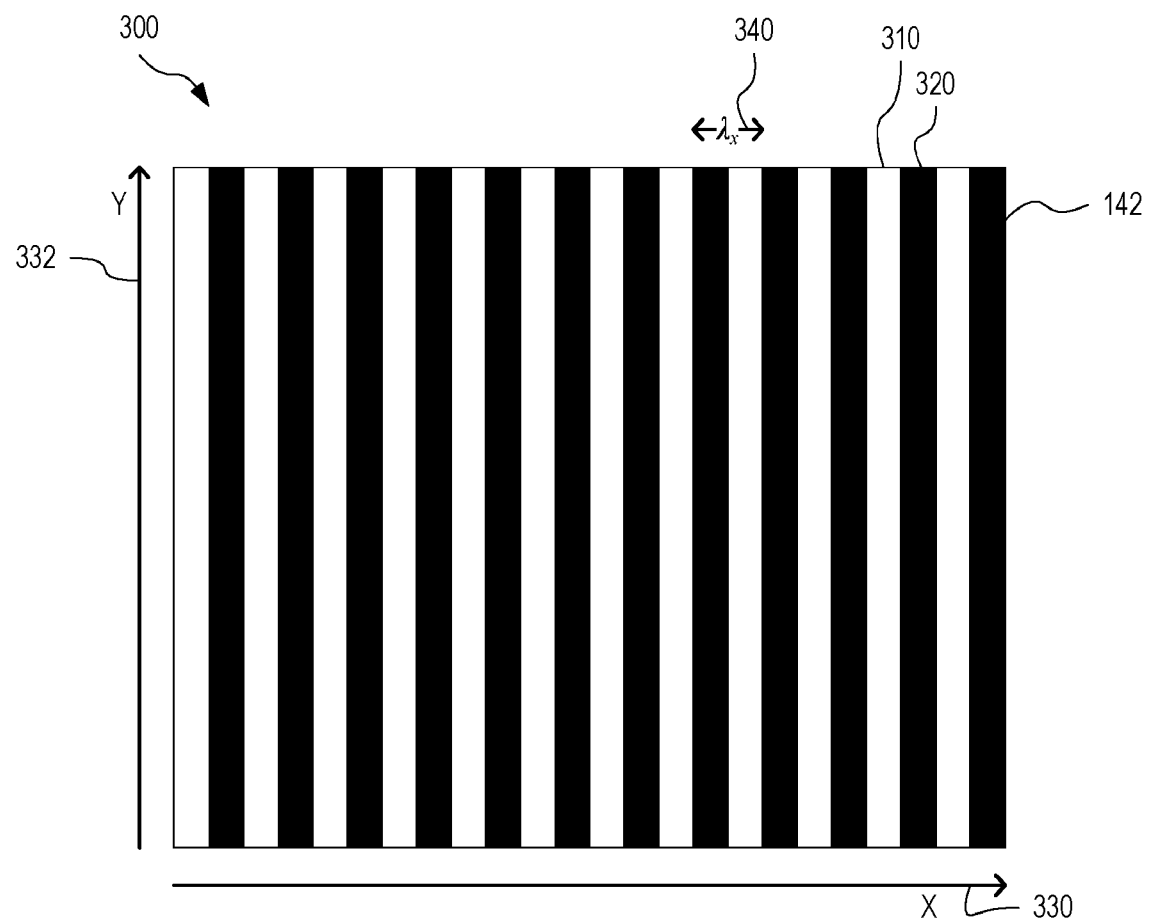
FIG. 8 is an illustration of structured light illumination at one spatial frequency.
Figure 8:
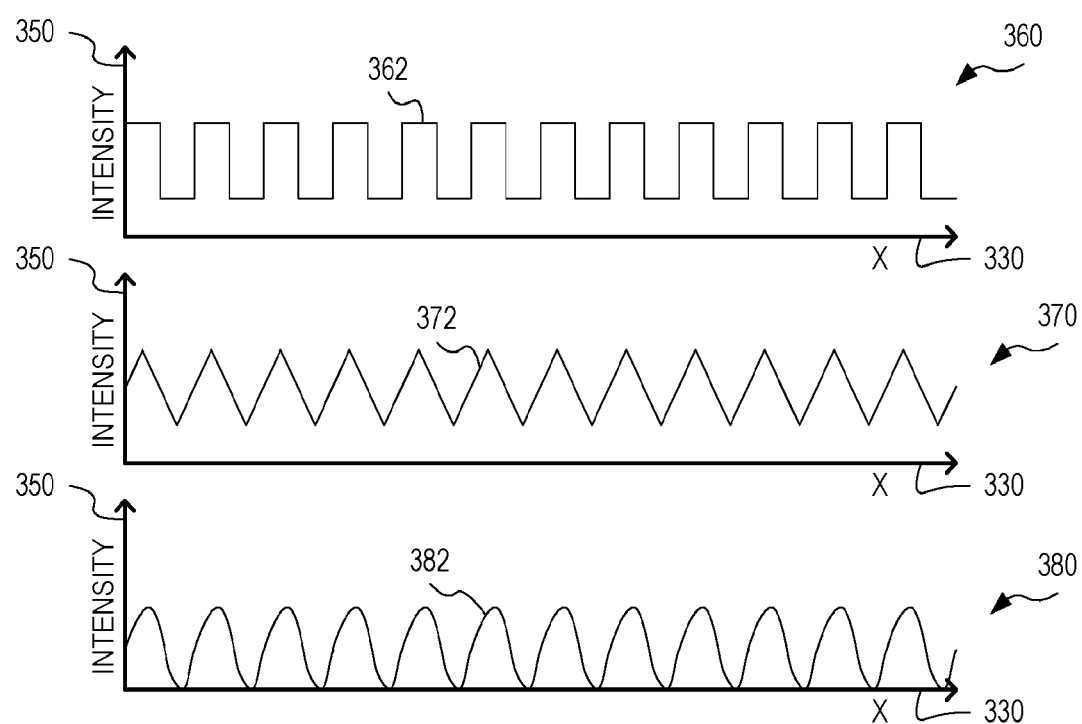
Figure 9:
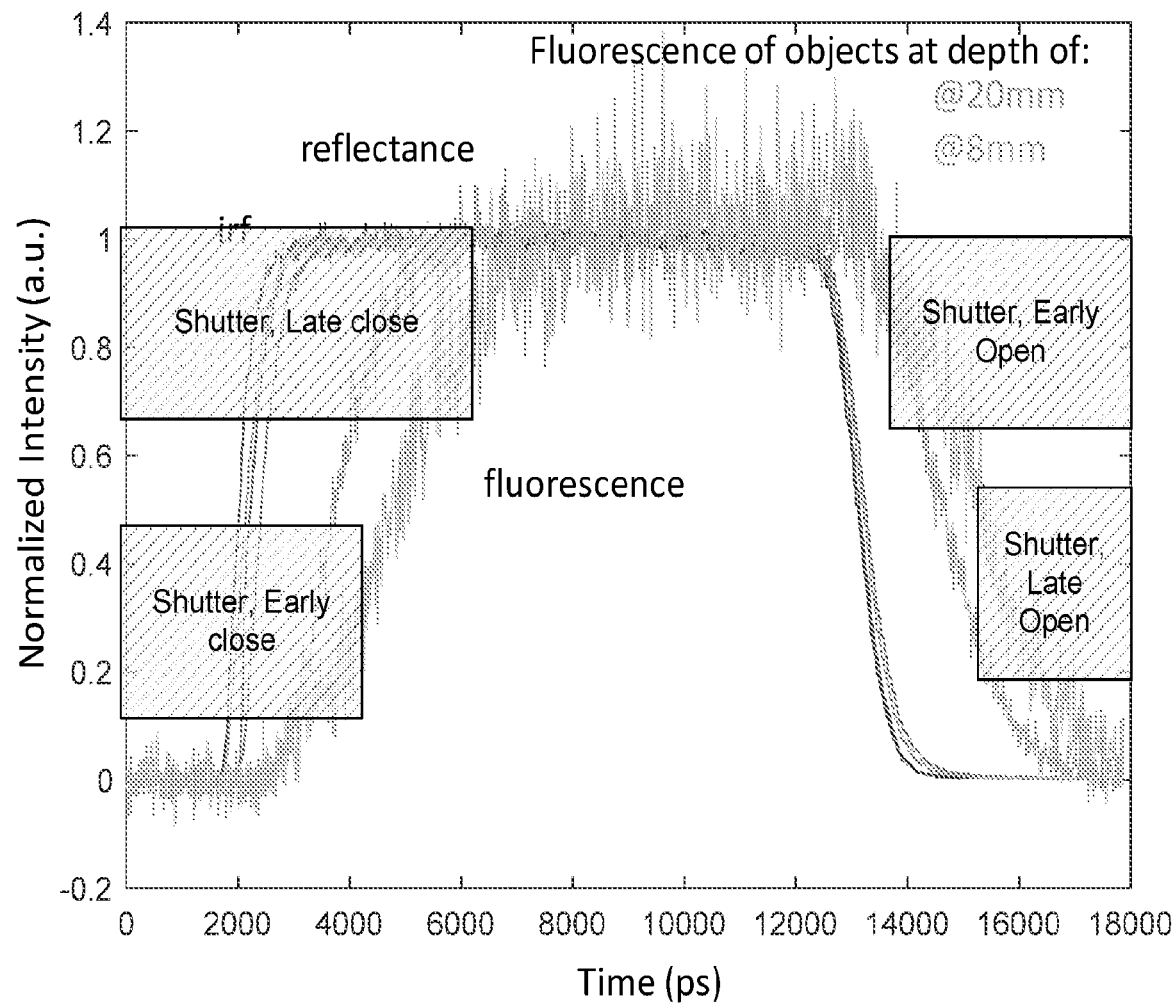
FIG. 9 is a graph illustrating reflected stimulus light and fluorescent emissions and turning-on and turning-off gate edges of a time-gated camera window, indicating how windows at different delay increments transitioning across a laser pulse can resolve fluorescent emissions from different depths in tissue.

Combining the above-described spatial modulation techniques using a spatial modulator as shown in FIG. 8 in conjunction with the pulsed laser and with the temporal modulation of a ToF sensor, provides another mechanism for resolving a subsurface depth of fluorescent object embedded in tissue. This uses a pulsed fluorescent stimulus light and a two-dimensional, time-of-flight, image sensor. FIG. 7 depicts a multimodal imaging system 800 as superficial SLI with a ToF sensor. A pulse timing unit 846 controls a pulsed laser 848 which, through lens system 850 illuminates a digital micromirror device (DMD) 852 to apply a spatial modulation to pulsed laser light. Pulsed laser light from DMD 852 is focused by lens system 854 onto tissue 860 A filter-changer 861 or tunable filter is between the tissue 860 and ToF gated camera 862 with settings for fluorescent imaging emissions-pass filter and a second setting that passes light of the stimulus wavelength so that optical properties of the tissue can be extracted using structured-light techniques from images obtained by camera 862. Pulse timing unit 846 controls timing of image capture by camera 862 An image processor 112 with memory 114, firmware 116, and display 118 and image storage is provided to reconstruct three-dimensional time-of-flight-based images from signals from ToF sensor, perform structured light optical parameter extraction, compensate for variable light path delays in the system, and provide tomographic images to the surgeon.

In another 3D reconstruction method, time-resolved fluorescence data are used with 3D inversion scheme for 3D fluorescence image reconstruction. The temporal information obtained with SPAD camera is used to reduce the ill-posedness of the 3D inverse problem.

In yet another reconstruction method, a 3D machine learning method such as a Convolutional Neural Network (CNN) or Generative adversarial network (GAN). Either a CNN or GAN is first trained on a set of either artificial or experimental time-resolved data, and then used with real time-resolved data to obtain a most likely 3D fluorophore distribution.

The inputs to CNN or GAN network comprise of temporal fluorescence image data from the SPAD sensor, and at least one dataset capturing the tissue optical properties (as determined through SFDI maps or temporal blur of diffuse reflectance in a stack of SPAD reflectance images), and a surface topology map, calculated from any of the aforementioned methods including in some embodiments from a stack of SPAD images.

The CNN or GAN network is trained with a large number of pseudo-random, computer-generated data that resemble the physical data. The training dataset includes simulation scenarios with multiple different tissue geometries, fluorophore distributions, and tissue optical properties. By solving a radiative transport equation, or by Monte Carlo method, resulting temporal fluorescence images, diffuse reflectance images, and SFDI images are calculated for each simulation scenario, and the neural network iteratively trained on this dataset.

After a training phase, CNN or GAN is implemented in software in the image processor with its inputs being the real experimental data streams created either offline, or streams that are updated in real time.

Since the CNN or GAN-network depth reconstruction may not preserve the signal power or fluorescence emissions brightness, and thus does not provide absolute concentration of fluorophore in fluorescent objects within tissue, the absolute fluorophore concentration can be calculated separately after determining depth. In these embodiments, fluorophore concentration is determined from detected fluorescence intensity, diffuse reflectance data giving stimulus-wavelength irradiation power, diffuse-reflectance-based tissue optical properties determined as described herein from time-blur of reflectance and/or spatially-modulated imaging, reconstructed depth, and expected fluorophore quantum yield.

FIG. 8 illustrates exemplary periodic spatial structure 300 of structured light 115 at an interrogation area. Periodic spatial structure 300 includes brighter regions 310 and darker regions 320. Brighter regions 310 and darker regions 320 alternate along an x-direction 330 to produce a characteristic spatial wavelength $\lambda_x$ (label 340) along x-direction 330. The spatial wavelength $\lambda_x$ (340) corresponds to a spatial frequency $f_x = \lambda_x^{-1}$ of periodic spatial structure 300.

Diagrams 360, 370, and 380 show exemplary line profiles of periodic spatial structure 300, plotted as intensity 350 along x-direction 330. Line-profile 362 of diagram 360 is rectangular, such that the intensity is high and substantially uniform within brighter regions 310, and low and substantially uniform within darker regions 320. Line profile 372 of diagram 370 is triangular, and line profile 382 of diagram 380 is sinusoidal.

Without departing from the scope hereof, periodic spatial structure 300 may be associated with other line profiles than rectangular, triangular, and sinusoidal. For example, periodic spatial structure 300 may have spatial structure, along x-direction 330, which is a superposition of rectangular, triangular, and/or sinusoidal. In addition, periodic spatial structure 300 may have any measurable, e.g., non-zero, contrast between brighter and darker regions 310 and 320, respectively, and the contrast between brighter and darker regions 310 and 320, respectively, may vary within the interrogation area. While FIG. 8 shows equal contribution to periodic spatial structure 300 from brighter regions 310 and darker regions 320, brighter regions 310 may occupy a majority of periodic spatial structure 300, or darker regions 320 may occupy a majority of periodic spatial structure 300. Furthermore, while FIG. 8 shows periodic spatial structure 300 as being constant in the y-direction 332, periodic spatial structure 300 may exhibit variation along y-direction 332 without departing from the scope hereof.

Figure 10A:
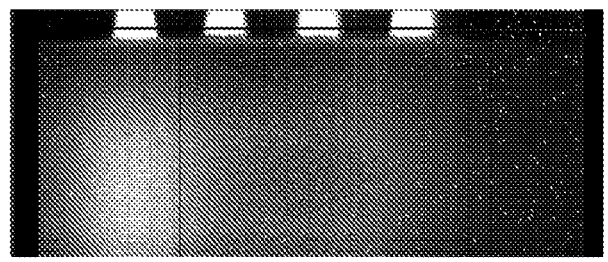
FIG. 10A represents 2D maps of steady-state fluorescence of 1 mL, "inclusions" of IRDye680 at different depths in a 1% intraiipid tissue phantom (as they would be seen by current clinical devices, but translated to black and white).
Figure 10B:
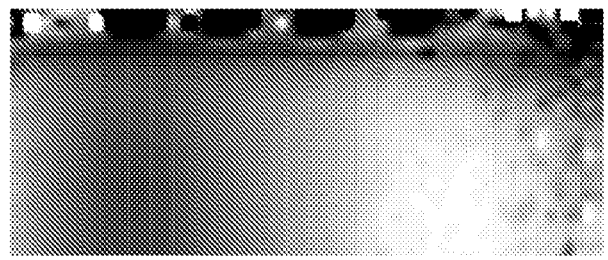
FIGS. 10B and 10C represent 2D maps of time offsets and Gaussian kernel widths obtained with the embodiment of FIG. 7.
Figure 10C:
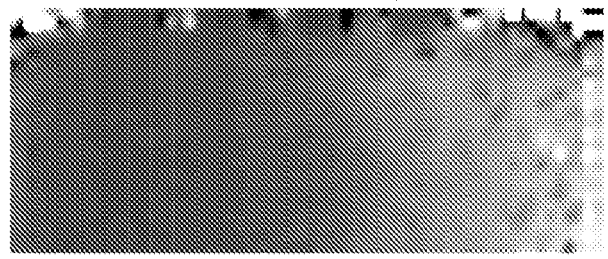

FIG. 10A illustrates exemplary 2D maps of steady-state fluorescence of 1 mL "inclusions" of IRDye680 at different depths in a 1% intralipid tissue phantom (as they would be seen by current clinical devices but translated to black and white). It somewhat shows the left, shallowest, inclusion, but there is no signal visible in the other three deeper inclusions. Further, FIGS. 10B and 10C, 2D illustrate maps of time offsets and Gaussian kernel widths. These parameters represent the parameters $C_2$ and $C_3$ in equations (1) and (2) but are evaluated with a simple Gaussian function to demonstrate the concept. For each pixel, we fitted a convolution of instrument response function with a Gaussian function, containing parameters mu and sigma. These are per pixel maps.

In an embodiment of an instrument 1200 (FIG. 11) adapted to perform ToF imaging, a pulsed laser 1202 provides pulses of less than 100 picoseconds width stimulus wavelength light through either a dispersive lens or scanner 1204 and an optional diverter 1206 and optional spatial modulator 1208 to a microscope optical system 1210 configured to project the light pulses onto tissue 1212. Tissue 1212 may but need not contain a fluorescent body 1214 containing a fast or medium-fast decay fluorophore. Microscope optical system 1210 is also configured to received light, both at the stimulus wavelength and at a fluorescent emissions wavelength, from tissue 1212 and pass received light through an optional diverter 1216 and a filter device 1218. In embodiments, the filter device 1218 is a filter-changer, in other embodiments filter device 1218 is an electrically-tunable optical filter.

Light passing through filter device 1218 passes through another optional diverter 1220 and into a high-speed, time-gated, electronic camera such as SPAD sensor 1222. SPAD sensor 1222 is configured to provide a sequence, or stack, of electronic image frames to image capture unit 1224 under control of pulse sequencer 1226. Pulse sequencer 1226 also control pulsed laser 1202 and is adapted to vary time relationship of a gate controlling SPAD sensor 1222 relative to pulses generated by pulsed laser 1202 in 10 picosecond steps.

The stack of electronic image frames is passed by image capture unit 1224 to image processor 1228 for digital image processing under control of code 1230 residing in memory 1232. Image processor 1228 performs calibrated surface profile determinations and image corrections as previously discussed and generates images for display-by-display processor 1234 on display 1236.

Embodiments equipped with optional emissions wavelength or white-light source 1238, diverter 1206, and spatial modulator 1208 are adapted to also perform structured light (or spatially modulated) light imaging of tissue to better define optical properties of tissue as may be needed for high resolution imaging of fluorescent bodies 1214 in tissue 1212. Embodiments equipped with diverter 1216, conventional eyepieces 1240, and ordinary-light illuminator LED's 1242 are adapted to permit proper positioning of the instrument by a surgeon over a surgical wound to view tissue and to allow the surgeon to view tissue 1212 surface in a manner like the way surgeons are used to viewing tissue. Embodiments equipped with digital camera 1244 and diverter 1220 are adapted to permit traditional fluorescent imaging, and to perform spatially-modulated imaging if spatial modulator 1208 is also provided.

Embodiments typically, but not always, include a database interface 1246 coupled to a remote database-serving host 1248 with a database in memory 1249 so that images may be stored in research and/or patient record databases and saved for post-surgical review.

Diverters as herein disclosed may, in some embodiments, be manual or electrically-operated mirrors adapted to pass light between a first port and a selected one of a second and third port. In alternative embodiments where light loss is not a concern, diverters may be replaced by beamsplitters.

In alternative embodiments, filter device 1218 and single SPAD sensor 1222 may be replaced by a beamsplitter or diverter coupled to pass light through an emissions wavelength passing but stimulus wavelength blocking filter to a SPAD sensor for fluorescent imaging, and through a stimulus wavelength passing filter to a second SPAD sensor or high speed digital camera for surface imaging and spatially-modulated imaging; such embodiments will, however, require additional calibration steps.

Figure 12:
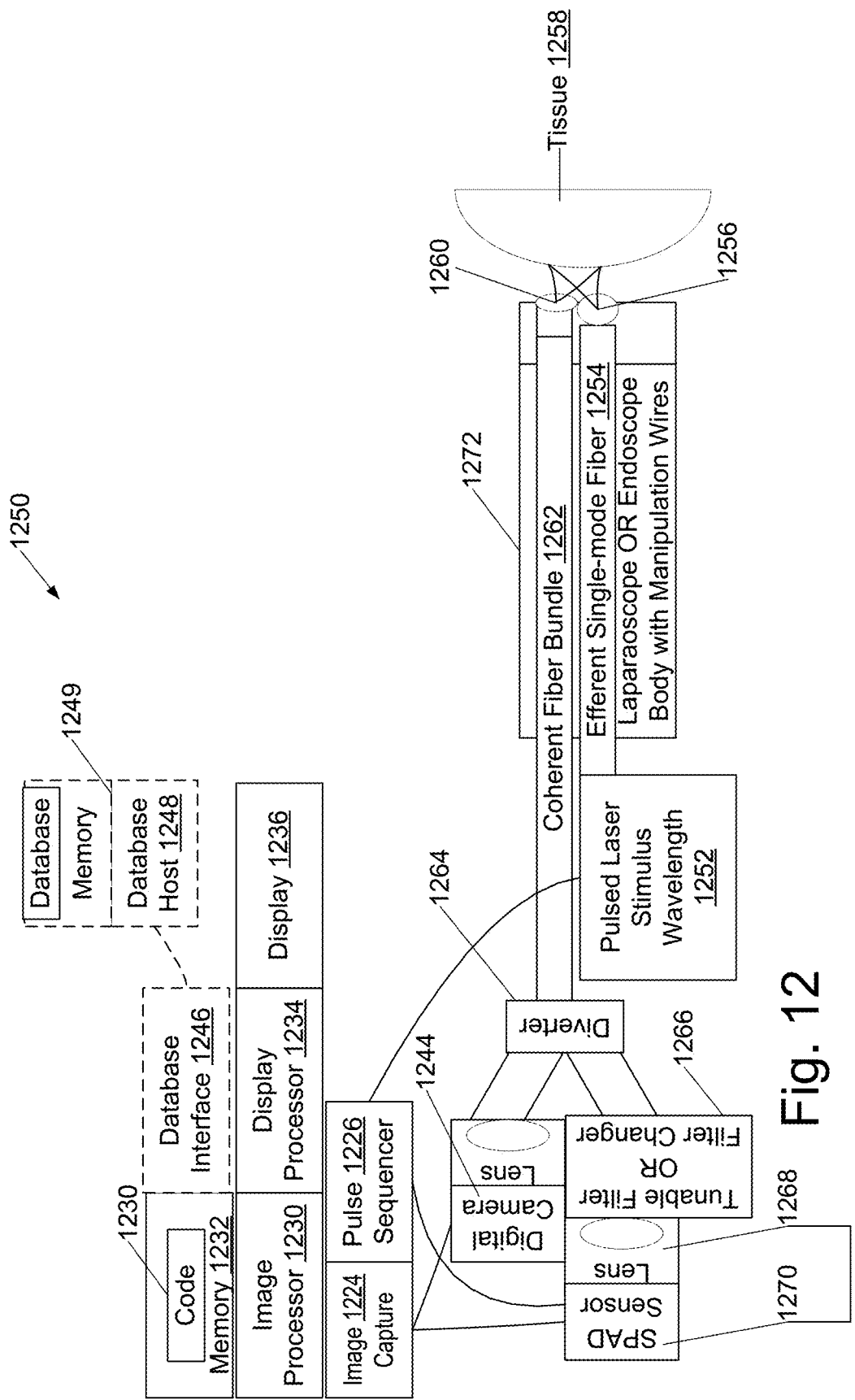
FIG. 12 is a block diagram of an embodiment incorporated into a laparoscope or endoscope system.

In an endoscopic embodiment 1250 (FIG. 12), pulsed laser 1252 is coupled to provide light pulses into efferent optical fiber 1254, efferent optical fiber 1254 is provides these pulses to a dispersive lens 1256 that is configured to illuminate tissue 1258 that may or may not contain a fluorescent body (not shown in FIG. 12). Light reflected from or scattered by, or emitted by fluorescence from, tissue 1258 and its fluorescent body is collected by an imaging lens 1260 and focused onto a distal end of a coherent fiber bundle 1262. Light passing through coherent fiber bundle 1262 is provided through a diverter 1264 and filter device 1266 to be focused by imaging lens 1268 onto a SPAD imager 1270 or other high-speed, gated, digital camera that provides digital image stacks to image capture unit. Coherent fiber bundle 1262 and efferent fiber 1254 run through endoscope or laparoscope body 1272 and may have length between one and eight feet according to the application. Blocks having a same reference number in FIG. 12 as in FIG. 11 perform similar functions and their descriptions are not repeated here for brevity.

In embodiments, the system of FIG. 11 or 12 is operated according the method 1400 of FIG. 14. Previously saved calibration data obtained according to the method of FIG. 13 and other methods, is read as it will be used. The instrument is positioned for imaging tissue, which may involve threading the endoscopic embodiment of FIG. 12 through body orifices or beginning a surgical procedure and positioning the microscopic embodiment of FIG. 11 over the surgical wound. Filter device 1218, 1266 is set to pass stimulus wavelengths. Laser pulses are then generated while sweeping image capture relative to laser pulse timing to capture a ToF image stack 1408. The ToF image stack and the saved calibration data are used to generate a map 1410 of the tissue surface, this surface map is then saved 1412. Time blurring of the reflected pulses is used to estimate optical properties of the tissue (not shown in FIG. 14).

In some embodiments, the laser is scanned across the tissue surface while images are captured, or multiple spatially-modulated patterns are projected onto the tissue surface while images are captured 1414, these images are analyzed to map optical properties of the surface 1416 at stimulus wavelengths.

Filter device 1218, 1266 is then set 1418 to pass fluorescent emissions wavelengths while blocking stimulus wavelength light.

In some embodiments, a white light illuminator or light from an emissions-wavelength laser is spatially-modulated and spatially-modulated patterns are projected onto the tissue surface while images are captured 1420, these images are analyzed to map optical properties of the surface 1422 at emissions wavelengths.

Laser pulses are then provided, with pulsewidth of less than a nanosecond and in an embodiment both risetime and pulsewidth of less than 100 picosecond, onto the tissue, while the gate for the SPAD sensor is swept in time to provide a ToF Fluorescent body SPAD image stack 1424. This is used to generate an initial ToF per-pixel delay map 1426, this initial ToF per-pixel delay map is corrected 1428 using the saved calibration data, and the map generated above in step 1410 is subtracted 1430 to provide a map of fluorescent emissions depth below the tissue surface. Corrections may then be applied 1432 using the maps of optical properties of the surface as generated in steps 1422, 1416, or as derived from time blur of reflectance images. The corrected depth map becomes 1434 a depth map of the fluorescent body and is then saved on the database server 1248 and displayed on display 1246 for use by a surgeon in completing surgery.

Combinations of Features

In embodiments, various features of the system herein described can be combined in a multitude of ways. Among combinations of features we anticipate are:

A system designated A for depth resolved imaging of fluorophore concentrations in tissue including a pulsed light source operable at a stimulus wavelength of the fluorophore concentrations and configured to illuminate the tissue, the pulsed light source configured to provide light pulses of less than one nanosecond in width; with at least one time gated electronic camera configured to generate reflectance images and fluorescent emissions images of the tissue, the time gated electronic camera configurable to image in time windows synchronized to pulses of the pulsed light source with time gate delay resolution of less than 100 picoseconds. A filter device is included configurable as a first filter having a passband for fluorescent emissions of the fluorophore concentrations while blocking light of the stimulus wavelength of the fluorophore concentrations, and as a second filter having a passband for light of the stimulus wavelength of the fluorophore concentrations. An image processor is included that is coupled to receive reflectance images and fluorescent emissions images from the time gated electronic camera, the image processor having a memory with firmware, the image processor configured to produce images incorporating depth information determined by time of flight of the light of the stimulus wavelength and the fluorescent emissions.

A system designated AA includes the system designated A with, in a light path from the pulsed light source, a structured-light modulator adaptable to provide a plurality of spatially modulated light patterns of the fluorescent stimulus light at a plurality of spatial frequencies and phase offsets.

A system designated AB includes the system designated A or AA where the filter device comprises a filter changer configured with a first and second filter.

A system designated AC includes the system designated A, or AA, wherein the filter device comprises a first filter disposed to filter light passing from tissue to a first time-gated camera of the at least one time gated electronic camera, and a second filter disposed to filter light passing from tissue to a second time gated electronic camera of the at least one time-gated camera.

A system designated AD including the system designated A, AA, AB, or AC wherein the image processor is configured to compensate the images incorporating information determined by time of flight for variations in optical path lengths to portions of the tissue.

A method designated B of resolving a subsurface depth of fluorescent object embedded in tissue, includes: measuring a reflectance temporal profile using a structured light modulator and a time of flight sensor to measure a time delay between a light pulse emission and a time of arrival of a reflected light pulse; determining a diffuse reflectance; measuring a fluorescence temporal profile; determining a diffuse fluorescence; extracting fluorescence depth parameters; and estimating depth from fluorescence depth parameters.

A method designated BA including the method designated B further including correcting intensity of fluorescence images using depth information, and correcting blur in a fluorescence image using depth information, and calculating fluorophore concentration based on corrected fluorescence intensity, and encoding depth and concentration to the image presented to a user.

A method designated BB including the method designated BA or B, wherein determining a diffuse reflectance further comprises performing a convolution of an instrument response function (IRF) according to:

$$I\_R \approx C\_1 t^{\wedge}(-3/2) \exp(-C\_2 t) \exp[(-C\_3/4)]$$

and extracting parameters $C_1$, $C_2$ and $C_3$.

A method designated BC including the method designated, BB, BA or B, wherein determining a diffuse fluorescence further comprises entering parameters C1, C2 and C3 in an equation $$I\_F \approx C\_1 t^{\wedge}(-3/2) \exp(-C\_2 t)[C\_4 \exp(-(C\_4/\wedge 2)/t) - C\_5 \exp(-(C\_3/\wedge 2)/t)]$$

and fitting a convolution with instrument reference factors to the fluorescence temporal profile.

A method designated BD including the method designated, BC, BB, BA or B, wherein a reflectance based tissue optical property measurement is used to calibrate a response of time of flight based depth of a map of tissue optical properties.

A method designated BE including the method designated, BD, BC, BB, BA or B, wherein the subsurface depth of the fluorescent object embedded in tissue is calculated for each pixel within a field of view of the time of flight sensor, using temporal profiles of fluorescence and diffuse reflectance, in conjunction with surface map.

A method designated BF including the method designated, BC, BD, BE, BB, BA or B, further including estimating fluorophore concentration and shape of the fluorescent object embedded in tissue, using the information provided by time of flight camera.

A method designated BG including the method designated, BC, BD, BE, BF, BB, BA or B, further including measuring a distance between the structured light modulator and the tissue, and between the time of flight sensor and the tissue to compensate for an inverse square law that governs excitation light transport.

A method designated BH including the method designated, BC, BD, BE, BF, BG, BB, BA or B where the light pulses are less than 100 picoseconds in width and the time gate delay resolution is less than 20 picoseconds.

An instrument for performing time of flight surface mapping and fluorescent depth estimation designated C includes a pulsed laser operable at a fluorescent stimulus wavelength coupled through a first optical device to provide illumination to an imaging optical system, the imaging optical system configured to provide light to tissue and to receive image light from the tissue; the imaging optical system coupled to provide image light through a filter device and to a single-photon avalanche detector (SPAD) image sensor, the SPAD image sensor coupled to provide high time resolution images to an image capture unit; an image processor coupled to receive images from the image capture unit and to process received images according to code in a memory and to provide images to a display; where the first optical device is selected from the group consisting of a lens configured to couple light to an efferent optical fiber, and a dispersive lens; where the pulsed laser provides pulses of less than 100 picoseconds risetime and less than 100 nanoseconds width, and the SPAD sensor has a gate time resolution of less than 100 picoseconds programmable by the image processor; where the image processor is configured by the code to set the filter device to pass the fluorescent stimulus wavelength, to receive a stimulus image stack comprising a plurality of SPAD images of the tissue taken at time increments of the SPAD sensor gate time resolution, to set the filter to pass a fluorescent emissions wavelength while blocking the fluorescent stimulus wavelength, to receive an emissions image stack comprising a plurality of SPAD images of the tissue taken at time increments of the SPAD sensor gate time resolution, to process the stimulus image stack into a surface map of the tissue, and to process the emissions image stack into a map of depth of fluorophore in the tissue; and where the imaging optical system is an optical system selected from a microscope optical system and an endoscope optical system.

An instrument for performing time of flight surface mapping and fluorescent depth estimation designated CA including the instrument for performing time of flight surface mapping and fluorescent depth estimation designated C where the imaging optical system comprises at least one efferent optical fiber, a dispersive lens configured to illuminate the tissue with light from the at least one efferent optical fiber, an imaging lens, and a coherent fiber bundle.

An instrument for performing time of flight surface mapping and fluorescent depth estimation designated CB including the instrument for performing time of flight surface mapping and fluorescent depth estimation designated CA or C wherein the at least one efferent optical fiber comprises a second coherent fiber bundle, and where a spatial modulator is coupled between the pulsed laser and the efferent optical fiber.

An instrument for performing time of flight surface mapping and fluorescent depth estimation designated CC including the instrument for performing time of flight surface mapping and fluorescent depth estimation designated CA, CB, or C where the imaging optical system is an optical microscopy optical system.

An instrument for performing time of flight surface mapping and fluorescent depth estimation designated CD including the instrument for performing time of flight surface mapping and fluorescent depth estimation designated CA, CB, CC, or C further comprising a diverter configured to couple light from the coherent fiber bundle to either the SPAD sensor or to a digital image sensor, the digital image sensor able to form images of light intensity.

An instrument for performing time of flight surface mapping and fluorescent depth estimation designated CE including the instrument for performing time of flight surface mapping and fluorescent depth estimation designated CA, CB, CC, CD, or C where the first optical device is coupled to the imaging optical system through a spatial modulator operable under control of the image processor, and where the image processor is configured to determine a map of optical properties of the tissue by configuring the spatial modulator to a plurality of spatial modulation patterns, obtaining digital images from a digital image sensor of tissue illuminated with the plurality of spatial modulation patterns, processing the digital images to determine the map of optical properties, and to use the map of optical properties to correct the map of depth of fluorophores in tissue.

An instrument for performing time of flight surface mapping and fluorescent depth estimation designated CF including the instrument for performing time of flight surface mapping and fluorescent depth estimation designated CA, CB, CC, CD, CE, or C where the first optical device is coupled to the imaging optical system through a spatial modulator A system designated ACA including the system designated A, AA, AB, AC, or AD, or the instrument designated C, CA, CB, CC, CD, CE, or CF, where time gate resolution is less than 20 picoseconds and pulses of the pulsed light source have pulsewidth of less than 100 picoseconds.

A system designated ACB including the system designated A, AA, AB, AC, ACA, or AD, or the instrument designated C, CA, CB, CC, CD, CE, or CF, wherein processing the emissions image stack into a map of depth of fluorophore in the tissue is performed using a previously-trained CNN or GAN neural network.

Changes may be made in the above methods and systems without departing from the scope hereof. It should thus be noted that the matter contained in the above description or shown in the accompanying drawings should be interpreted as illustrative and not in a limiting sense. Herein, and unless otherwise indicated: (a) the adjective "exemplary" means serving as an example, instance, or illustration, and (b) the phrase "in embodiments" is equivalent to the phrase "in certain embodiments," and does not refer to all embodiments. The following claims are intended to cover all generic and specific features described herein, as well as all statements of the scope of the present method and system, which, as a matter of language, might be said to fall therebetween.

What is claimed is:

1. A system for depth resolved imaging of fluorophore concentrations in tissue comprising:
   a pulsed light source operable at a stimulus wavelength of the fluorophore concentrations and configured to illuminate the tissue, the pulsed light source configured to provide light pulses of less than one nanosecond in width;
   at least one time gated electronic camera configured to generate reflectance images and fluorescent emissions images of the tissue, the time gated electronic camera configurable to image in time windows synchronized to pulses of the pulsed light source with time gate delay resolution of less than 100 picoseconds;

a filter device in a light path of the pulsed light source that is configurable as a first filter having a passband for fluorescent emissions of the fluorophore concentrations while blocking light of the stimulus wavelength of the fluorophore concentrations, and as a second filter having a passband for light of the stimulus wavelength of the fluorophore concentrations; and an image processor coupled to receive reflectance images and fluorescent emissions images from the time gated electronic camera, the image processor having a memory with firmware, the image processor configured to produce images incorporating depth information determined by time of flight of the light of the stimulus wavelength and the fluorescent emissions.

2. The system of claim 1 wherein the pulsed light source comprises a structured-light modulator adaptable to provide a plurality of spatially modulated light patterns at a plurality of spatial frequencies and phase offsets.

3. The system of claim 2 wherein the image processor is configured to compensate the images incorporating information determined by time of flight for variations in optical path lengths to portions of the tissue.

4. The system of claim 1 where the filter device comprises a filter changer configured with a first filter and a second filter.

5. The system of claim 1 wherein the filter device comprises a first filter disposed to filter light passing from tissue to a first time-gated camera of the at least one time gated electronic camera and comprises a second filter disposed to filter light passing from tissue to a second time gated electronic camera of the at least one time-gated camera.

6. The system of claim 1 where the light pulses are less than 100 picoseconds in width and the time gate delay resolution is less than 20 picoseconds.

7. The system of claim 1 where time gate resolution is less than 20 picoseconds and pulses of the pulsed light source have pulsewidth of less than 100 picoseconds.

8. The system of claim 1 where the at least one time gated electronic camera comprises an image sensor selected from the group consisting of: single-photon avalanche detector (SPAD) image sensor, a time-gated complementary metal-oxide semiconductor (CMOS) sensor, and an intensified CMOS sensor.

9. The system of claim 1 wherein the pulsed light source provides pulses of less than 100 picoseconds risetime and less than 100 nanoseconds width.

10. The system of claim 1 wherein the time gated electronic camera has a gate time resolution of less than 100 picoseconds programmable by the image processor.

* * * * *